United States Patent

Rosenau et al.

Patent Number: 5,917,060
Date of Patent: Jun. 29, 1999

[54] PREPARATION OF CHROMANYL DERIVATIVES

[75] Inventors: Thomas Rosenau, Eisenach; Wolf-Dieter Habicher, Dresden, both of Germany

[73] Assignee: BASF Aktiengesellschaft, Ludwigshafen, Germany

[21] Appl. No.: 08/992,539

[22] Filed: Dec. 17, 1997

[51] Int. Cl.[6] .................................................. C07C 311/04
[52] U.S. Cl. ........................... 549/408; 549/410; 549/412
[58] Field of Search ..................................... 549/412, 408, 549/410

[56] References Cited

PUBLICATIONS

Gilbert et al, J. Chem. Soc. Perkin Trans, 2, "Reactions of Carboxyl radicals generated by photocleavage . . ." pp. 511–518, (1996).
Rosenau et al, Synlett, "Novel Tocopherol Comps, VII γ–Tocopherol–5–carboxylic acid" pp. 208–210 (1997).
March, Advanced Organic Chemistry, 3rd ed. pp. 507–508 1974.
Rosenau et al, Tetrahedron, vol. 51 No. 29 "Novel Tocopherol Compound" pp. 7919–7920, 1995.
Dyke, The Chemistry of the Vitiamis, vol. VI, pp. 256–257 (1965).

*Primary Examiner*—John Kight
*Assistant Examiner*—Raymond Covington
*Attorney, Agent, or Firm*—Keil & Weinkauf

[57] ABSTRACT

A process for the preparation of chromanyl derivatives of the formula I

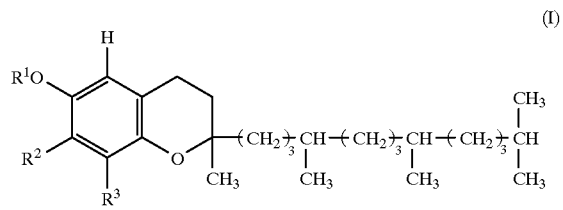

where $R^1$ is hydrogen, $C_1$–$C_8$-alkyl, aryl, aralkyl, $Si(R^4)_3$, $C(=O)R^4$ or $C_1$–$C_4$-alkoxymethyl, $R^2$ and $R^3$ are hydrogen or $C_1$-$C_3$-alkyl, and $R^4$ is $C_1$–$C_8$-alkyl or aryl, which comprises decarboxylating 5-carboxychromanyl derivatives of the formula II

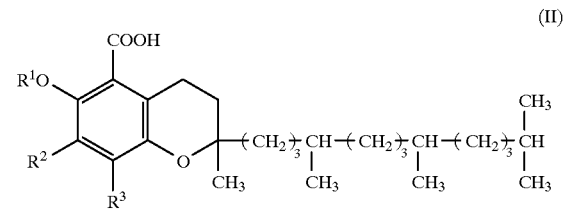

where the substituents $R^1$ to $R^3$ are as defined above and 5-carboxylchromanyl derivatives of the formula II.

11 Claims, No Drawings

PREPARATION OF CHROMANYL DERIVATIVES

The present invention relates to a process for the preparation of chromanyl derivatives of the formula I

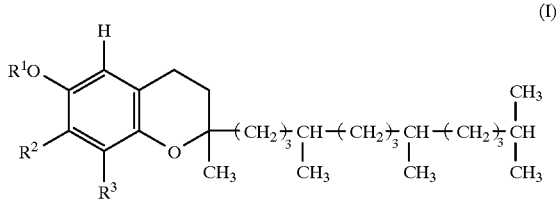

(I)

where
$R^1$ is hydrogen, $C_1$–$C_8$-alkyl, aryl, aralkyl, $Si(R^4)_3$, $C(=O)R^4$ or $C_1$–$C_4$-alkoxymethyl,
$R^2$ and $R^3$ are hydrogen or $C_1$–$C_3$-alkyl, and
$R^4$ is $C_1$–$C_8$-alkyl or aryl,
which comprises decarboxylating 5-carboxychromanyl derivatives of the formula II

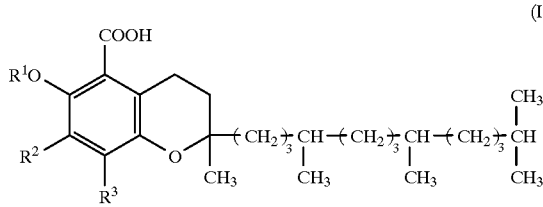

(II)

where $R^1$ to $R^3$ are as defined above.

Vitamin E is a general name for tocopherol and tocotrienol. Racemic α-tocopherol is a large-scale industrial product which is used as an antioxidant in many different areas of application, for example in the food/pharmaceutical sector or as an animal feed additive (B. Halliwell, J. M. C. Gutteridge, Free Radicals in Biology and Medicine, Oxford University Press, New York, 1989; L. Machlin, Vitamin E in Health and Diseases, Marcel Dekker Inc., Ed. L. Packer and J. Fuchs, New York, 1993) and also as a stabilizer in plastics (DE-A 11 14 319, EP-A-0 036 169, EP-A-0 704 477).

γ-Tocopherol and δ-tocopherol, besides α-tocopherol the most important components of natural vitamin E mixtures, have hitherto been available only by isolation from natural sources, for example by extraction from vegetable oils. An economical production process for γ- and δ-tocopherol has hitherto not been described.

It is an object of the present invention to provide a novel process for the preparation of chromanyl derivatives, in particular of γ- and δ-tocopherol and derivatives thereof.

We have found that this object is achieved by the process defined at the beginning.

The chromanyl derivatives of the formula I preferably prepared by the aforementioned process are those where
$R^1$ is hydrogen, benzyl, o-nitrobenzyl or $C(=O)R^4$, where $R^4$ is $C_1$–$C_8$-alkyl or aryl, and
$R^2$ and $R^3$ are $CH_3$,
and also the chromanyl derivatives of the formula I where
$R^1$ is hydrogen, benzyl, o-nitrobenzyl or $C(=O)R^4$, where $R^4$ is $C_1$–$C_8$-alkyl or aryl, and
$R^2$ is hydrogen and
$R^3$ is $CH_3$.

The aforementioned chromanyl derivatives of the formulae I and II can be either racemic compounds, for example derivatives of D,L-α-tocopherol, or else optically active compounds, for example derivatives of R,R,R-α-tocopherol.

Chromanyl derivatives of the formula II where $R^1$ is hydrogen or acetyl and $R^2$ and $R^3$ are both methyl are described by T. Rosenau and W. D. Habicher in Synlett, 1997, 208.

Alkyl radicals which may be mentioned for $R^1$ and $R^4$ are branched or unbranched $C_1$–$C_8$-alkyl chains, such as methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl and 2-ethylhexyl.

Preferred alkyl radicals for $R^1$ and $R^4$ are branched or unbranched $C_1$–$C_4$-alkyl chains, such as methyl, ethyl, n-propyl and isopropyl, n-butyl, 1-methylpropyl, 2-methylpropyl and 1,1-dimethylethyl.

Alkyl radicals which may be mentioned for $R^2$ and $R^3$ are branched or unbranched $C_1$–$C_3$-alkyl chains, such as methyl, ethyl, n-propyl, isopropyl and, in particular, methyl.

For the purposes of the present invention, aryl for $R^1$ and $R^4$ is taken to mean aromatic rings or ring systems having 6 to 18 carbon atoms in the ring system, for example phenyl or naphthyl, which may be substituted by one or more radicals, such as halogen, eg. fluorine, chlorine or bromine, cyano, nitro, amino, $C_1$–$C_4$-alkylamino, for example methylamino, ethylamino, n-propylamino, isopropylamino or n-butylamino, hydroxyl, $C_1$–$C_4$-alkyl, for example methyl, ethyl, n-propyl, isopropyl or n-butyl, $C_1$–$C_4$-alkoxy, for example methoxy, ethoxy, n-propoxy, isopropoxy or other radicals. Preference is given to phenyl, substituted phenyl, such as methoxyphenyl, and naphthyl.

Possible aralkyl radicals for $R^1$ are $C_1$–$C_4$-alkylenephenyl or $C_1$–$C_4$-alkylenenaphthyl, in which the aromatic ring systems may be substituted by one or more further radicals, such as halogen, eg. fluorine, chlorine or bromine, cyano and nitro, and in which $C_1$–$C_4$-alkylene is inter alia methylene, ethylene, n-propylene, isopropylene or n-butylene. Preferred aralkyl radicals are benzyl and o-nitrobenzyl.

Possible alkoxymethyl radicals for $R^1$ are $C_1$–$C_4$-alkoxymethyl radicals, in particular methoxymethyl and methoxyethoxymethyl.

Surprisingly, we have now succeeded in removing the carboxyl function from the compounds of the formula II in a simple manner to give, in particular, derivatives of γ- and δ-tocopherol.

The decarboxylation can be carried out either chemically or, preferably, photochemically.

The chemical decarboxylation can be carried out thermally or under basic conditions by processes known per se, as are described, for example, by J. March "Advanced Organic Chemistry", published by John Wiley, New York, 3rd Edition 1985, p. 507 et seq. and also in Ullmanns Encyklopädie der technischen Chemie [Ullmanns Encyclopedia of Industrial Chemistry], Urban & Schwarzenberg, Munich, 3rd Edition 1962, Vol. 13, p. 84 to 94.

The photochemical decarboxylation is carried out by methods known per se, as are described, for example, by B. C. Gilbert et al., J. Chem. Soc., Perkin Trans. 2, 1996, 4, 511; K. Park et al., Bull. Korean Chem. Soc. 1991, 12, 438 and I. Izumi et al., J. Phys. Chem. 1981, 85, 218.

In a preferred embodiment, a solution of the chromanyl derivatives of the formula II in an organic solvent, for example in a mixture of benzene and methanol, is irradiated with short-wave light in the presence of a photosensitizer, for example 1,10-phenanthrolinyliron(III) complex. Examples of the light source are an $N_2$ laser having a wavelength in the range from 300 to 350 nm and a high pressure mercury lamp.

Irradiation is carried out at from −20° C. up to the boiling point of the solvent, preferably in the range from −20 to 50° C., particularly preferably from 10 to 20° C.

The reaction time is from 5 min to 5 h, preferably from 30 min to 3 h.

Following decarboxylation, the reaction mixture is worked up using customary methods, for example by extraction and, in some instances, by distillation or chromatographic purification.

The present invention also relates to 5-carboxychromanyl derivatives of the formula II

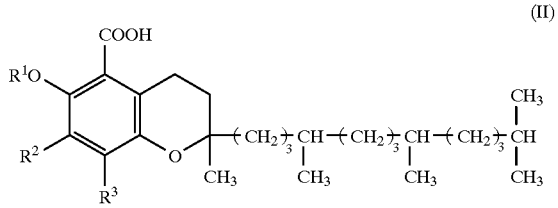

where
$R^1$ is hydrogen, $C_1-C_8$-alkyl, aryl, aralkyl, $Si(R^4)_3$, $C(=O)R^4$ or $C_1-C_4$-alkoxymethyl,
$R^2$ and $R^3$ are hydrogen or $C_1-C_3$-alkyl, and
$R^4$ is $C_1-C_8$-alkyl or aryl.

Preferred chromanyl derivatives of the formula II are those where
$R^1$ is hydrogen, benzyl, o-nitrobenzyl or $C(=O)R^4$, where $R^4$ is $C_1-C_8$-alkyl or aryl, and
$R^2$ and $R^3$ are $CH_3$,
and also the chromanyl derivatives of the formula II where
$R^1$ is hydrogen, benzyl, o-nitrobenzyl or $C(=O)R^4$, where $R^4$ is $C_1-C_8$-alkyl or aryl,
$R^2$ is hydrogen and
$R^3$ is $CH_3$.

The present invention further relates to a process for the preparation of 5-carboxychromanyl derivatives of the formula II, which comprises oxidizing 5-halomethylchromans of the formula III

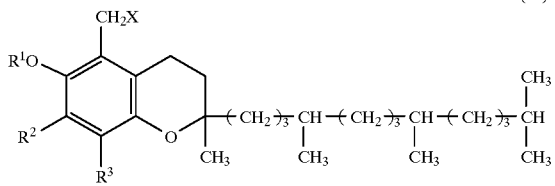

where $R^1$ to $R^3$ are as defined above, and X is halogen, in particular Br or Cl.

The 5-halomethylchromans of the formula III used as starting compounds for the novel process are known compounds (T. Rosenau, W. D. Habicher, Tetrahedron, 1995, 51, 7919) and can, for example, be prepared selectively by bromination or chlorination of the 5-methyl group of vitamin E or derivatives thereof in inert organic solvents, such as hydrocarbons or ethers, for example hexane, heptane or octane.

The preparation of the compounds of formula II preferably involves protecting the phenolic OH function prior to oxidation of the benzylic $CH_2$-X group (X=halogen). This is advantageously effected by conventional, acid-catalyzed insertion of a protective group, in particular by acid-catalyzed acylation. It is, however, also possible to use other protective groups for the phenolic OH group, including those described by T. W. Greene and P. G. M. Wuts in "Protective Groups in Organic Synthesis, John Wiley & Sons, Inc., New York (1991) p. 143 to 175.

The 5-halomethylchromans, in particular the acylated 5-bromomethylchromans of the formula III, can be converted into the chromanyl derivatives of the formula II using conventional oxidizing agents, described inter alia in "Organikum", Barth Verlagsgesellschaft, 19th Edition, 1993, p. 361 to 399.

The optimum pH for the chosen oxidizing agent is set by adding acids or bases.

In a particular embodiment, the oxidation is carried out using potassium permanganate under phase transfer conditions in a mixture of water and a water-immiscible organic solvent, for example hexane, heptane, octane, toluene, propylene carbonate or chlorinated hydrocarbons, preferably $CH_2Cl_2$, in the presence of a phase transfer catalyst, eg. tetrabutylammonium chloride, at from −20 to +40° C., preferably from −10 to +10° C.

The reaction time is generally in the range from 5 min to 5 h, preferably in the range from 10 min to 2 h.

The amount of oxidizing agent is heavily dependent on the type of oxidizing agent. If potassium permanganate is used under acid conditions, advantageously prom 0.5 to 2 mol, in particular 0.7 to 1.5 mol, of potassium permanganate are used per mole of compound III.

Following oxidation, the reaction mixture is worked up by customary methods, for example by extraction with $CH_2Cl_2$ and, in some instances, chromatographic purification.

The present invention further relates to a process for the preparation of chromanyl derivatives of the formula I

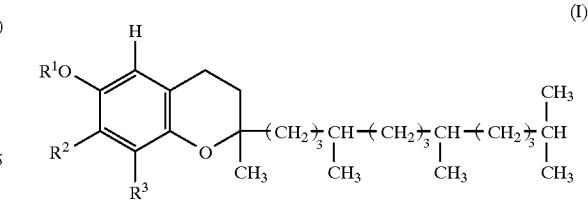

where
$R^1$ is hydrogen, $C_1-C_8$-alkyl, aryl, aralkyl, $Si(R^4)_3$, $C(=O)R^4$ or $C_1-C_4$-alkoxymethyl,
$R^2$ and $R^3$ are hydrogen or $C_1-C_3$-alkyl, and
$R^4$ is $C_1-C_8$-alkyl or aryl, which comprises, in a first process step, oxidizing 5-halomethylchromanyl derivatives of the formula III

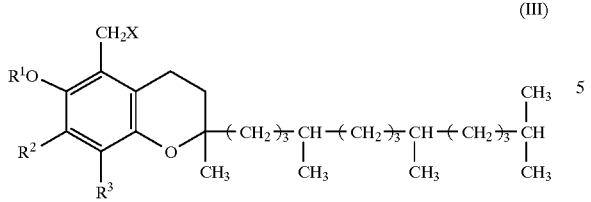

(III)

where the substituents $R^1$ to $R^3$ are as defined above, and X is halogen, to give the 5-carboxychromanyl derivatives of the formula II

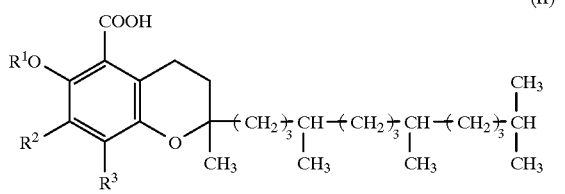

(II)

where the substituents $R^1$ to $R^3$ are as defined above, and, in a second process step, decarboxylating the compounds of the formula II to give the chromanyl derivatives of the formula I.

For a more precise definition of the substituents $R^1$ to $R^4$ and also for specific variants of the individual process steps, reference is made to the description already given above.

The following examples serve to illustrate the novel process in more detail.

EXAMPLE 1

A solution of 5a-bromo-α-tocopherol (1.528 g, 3 mmol) in a mixture of 10 ml of $CH_2Cl_2$, 10 ml of glacial acetic acid, 2 ml of acetic anhydride and 0.1 ml of conc. sulfuric acid was stirred for 12 h under a protective gas at room temperature. 50 ml of water and 50 ml of $CH_2Cl_2$ were then added and the reaction mixture was stirred for a further 30 min. After cooling to 0° C. and adding 0.4 g (2.53 mmol) of potassium permanganate in 10 ml of water and 0.083 g (0.3 mmol) of tetrabutylammonium chloride, the phases were separated after a reaction time of 15 min at 0° C. The organic phase was washed with 10 ml of a 1N aqueous HCl solution and then with water. After the solvent had been distilled off, the residue was taken up in a mixture of 50 ml of methanol and 10 ml of conc. HCl, refluxed for 1 h, then diluted with 100 ml of water and again taken up in $CH_2Cl_2$. The $CH_2Cl_2$ solution was washed with 1N aqueous NaOH solution and then with 1N aqueous HCl, and dried over $Na_2SO_4$. Distilling off the solvent gave γ-tocopherol-5-carboxylic acid as a pale yellow viscous oil in a yield of 82%. $^1$H-NMR (300 MHz, $CDCl_3$, $CD_3COOD$): δ 2.08 (s, 3H, Ar—$CH_3$); 2.10 (s, 3H, Ar—$CH_3$); 2.59 (t, 2H, Ar—$CH_2$—). The resonance signals of the isoprenoid side chain below 2 ppm are not listed separately.

EXAMPLE 2

0.46 g (1 mmol) of γ-tocopherol-5-carboxylic acid and 0.0023 g ($10^{-5}$ mol) of 1,10-phenanthrolinyliron(III) complex in 100 ml of a degassed benzene/methanol mixture (1:1, v/v) were irradiated from the outside for 1 h at 20° C. in a photoreactor fitted with a thermostat and a pump circulation system using an $N_2$ laser (337 nm). The reaction mixture was then diluted with n-hexane and chromatographed on an aluminum oxide column. γ-Tocopherol was obtained in a yield of 72%.

We claim:

1. A process for preparation of chromanyl derivatives of the formula I

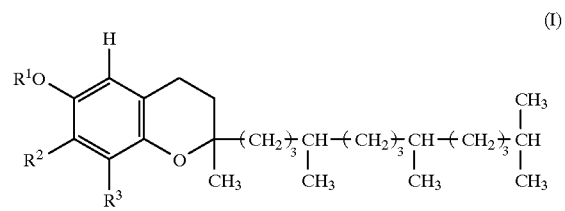

(I)

where
   $R^1$ is hydrogen, $C_1$–$C_8$-alkyl, aryl, aralkyl, $Si(R^4)_3$, $C(=O)R^4$ or $C_1$–$C_4$-alkoxymethyl,
   $R^2$ and $R^3$ are hydrogen or $C_1$–$C_3$-alkyl, and
   $R^4$ is $C_1$–$C_8$-alkyl or aryl,
which comprises decarboxylating 5-carboxychromanyl derivatives of the formula II

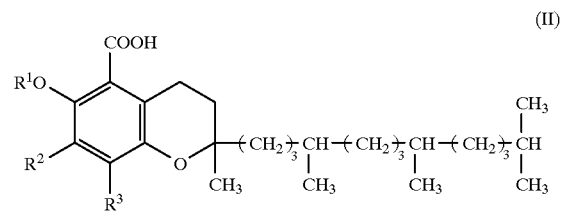

(II)

where the substituents $R^1$ to $R^3$ are as defined above.

2. The process of claim 1, wherein
   $R^1$ is hydrogen, benzyl, o-nitrobenzyl or $C(=O)R^4$, where $R^4$ is $C_1$–$C_8$-alkyl or aryl, and
   $R^2$ and $R^3$ are $CH_3$.

3. The process of claim 1, wherein
   $R^1$ is hydrogen, benzyl, o-nitrobenzyl or $C(=O)R^4$, where $R^4$ is $C_1$–$C_8$-alkyl or aryl,
   $R^2$ is hydrogen and
   $R^3$ is $CH_3$.

4. The process of claim 1, wherein the decarboxylation is carried out photochemically.

5. 5-Carboxychromanyl derivatives of the formula II

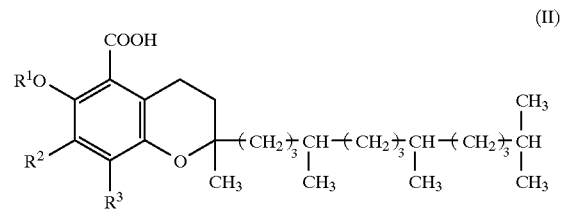

(II)

where
   $R^1$ is hydrogen, $C_1$–$C_8$-alkyl, aryl, aralkyl, $Si(R^4)_3$, $C(=O)R^4$ or $C_1$–$C_4$-alkoxymethyl,
   $R^2$ and $R^3$ are hydrogen or $C_1$–$C_3$-alkyl, and
   $R^4$ is $C_1$–$C_8$-alkyl or aryl.

6. 5-Carboxychromanyl derivatives of the formula II as defined in claim 5, where
   $R^1$ is hydrogen, benzyl, o-nitrobenzyl or $C(=O)R^4$, where $R^4$ is $C_1$–$C_8$-alkyl or aryl, and
   $R^2$ and $R^3$ are $CH_3$.

7. 5-Carboxychromanyl derivatives of the formula II as defined in claim 5, where $R^1$ is hydrogen, benzyl, o-nitrobenzyl or C(=O)$R^4$, where $R^4$ is $C_1$–$C_8$-alkyl or aryl, $R^2$ is hydrogen and $R^3$ is $CH_3$.

8. A process for the preparation of 5-carboxychromanyl derivatives of the formula II as defined in claim 5, which comprises oxidizing a 5-halomethylchroman of the formula III

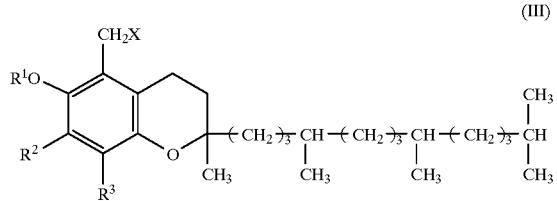

where the substituents $R^1$ to $R^3$ are as defined in claim 5 and X is halogen.

9. The process of claim 8, wherein $R^1$ is hydrogen, benzyl, o-nitrobenzyl or C(=O)$R^4$, where $R^4$ is $C_1$–$C_8$-alkyl or aryl, $R^2$ and $R^3$ are $CH_3$, and X is Br or Cl.

10. The process of claim 8, wherein $R^1$ is hydrogen, benzyl, o-nitrobenzyl or C(=O)$R^4$, where $R^4$ =$C_1$–$C_8$-alkyl or aryl, $R^2$ is hydrogen, $R^3$ is $CH_3$, and X is Br or Cl.

11. A process for the preparation of chromanyl derivatives of the formula I

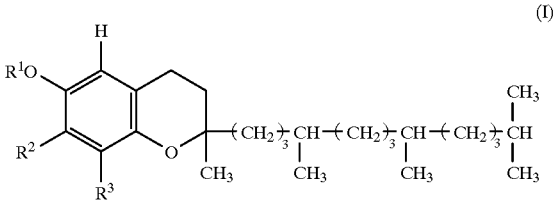

where $R^1$ is hydrogen, $C_1$–$C_8$-alkyl, aryl, aralkyl, Si($R^4$)$_3$, C(=O)$R^4$ or $C_1$–$C_4$-alkoxymethyl, $R^2$ and $R^3$ are hydrogen or $C_1$–$C_3$-alkyl, and $R^4$ is $C_1$–$C_8$-alkyl or aryl, which comprises, in a first process step, oxidizing 5-halomethylchromanyl derivatives of the formula III

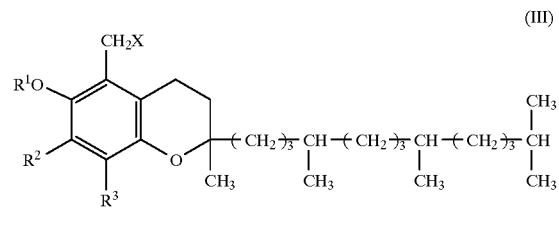

where the substituents $R^1$ to $R^3$ are as defined above, and X is halogen, to give the 5-carboxychromanyl derivatives of the formula II

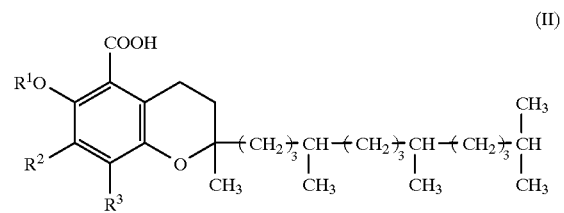

where the substituents $R^1$ to $R^3$ are as defined above, and, in a second process step, decarboxylating the compounds of the formula II to give the chromanyl derivatives of the formula I.

* * * * *